US00PP26574P2

(12) United States Plant Patent
Sakai

(10) Patent No.: US PP26,574 P2
(45) Date of Patent: Apr. 5, 2016

(54) ***JACARANDA* TREE NAMED 'SAKAI01'**

(50) Latin Name: *Jacaranda mimosifolia*
Varietal Denomination: Sakai01

(71) Applicant: Kiyoshi Sakai, Miyazaki (JP)

(72) Inventor: Kiyoshi Sakai, Miyazaki (JP)

( * ) Notice: Subject to any disclaimer, the term of this patent is extended or adjusted under 35 U.S.C. 154(b) by 144 days.

(21) Appl. No.: 14/120,549

(22) Filed: Jun. 2, 2014

(51) Int. Cl.
*A01H 5/02* (2006.01)

(52) U.S. Cl.
USPC ..... Plt./216

(58) Field of Classification Search
USPC ..... Plt./216
See application file for complete search history.

*Primary Examiner* — Anne Grunberg
(74) *Attorney, Agent, or Firm* — Penny J. Aguirre

(57) ABSTRACT

A new cultivar of *Jacaranda mimosifolia*,'Sakai01', that is characterized by its dwarf plant habit, its slow growth habit, its ability to flower on two year-old plants, and its flowers that are violet in color.

2 Drawing Sheets

Botanical classification: *Jacaranda mimosifolia.*
Varietal denomination: 'Sakai01'.

BACKGROUND OF THE INVENTION

The present invention relates to a new and distinct cultivar of *Jacaranda mimosifolia* and will be referred to hereafter by its cultivar name, 'Sakai01'. 'Sakai01' represents a new sub-tropical tree grown for landscape use.

The Inventor discovered the new cultivar, 'Sakai01', as a chance seedling in his garden in Nichinan-shi, Miyazaki, Japan in May 1995. In comparison to other seedlings of *Jacaranda mimosifolia* he had observed, the new cultivar was dwarf in habit. Subsequent to grafting he made the additional observation that the new cultivar produced flowers only 2 years after grafting.

Asexual propagation of the new cultivar was first accomplished by the Inventor by budding and grafting in Nichinan-shi, Miyazaki, Japan in May 1997. Asexual propagation by budding and grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Sakai01', as a unique from all cultivar of *Jacaranda mimosifolia.*

1. 'Sakai01' exhibits a dwarf plant habit.
2. 'Sakai01' exhibits a slow growth habit.
3. 'Sakai01' exhibits flowering on two year-old plants.
4. 'Sakai01' exhibits flowers that are violet in color.

The parent plant of 'Sakai01', an unnamed *Jacaranda mimosifolia* plant, differs from 'Sakai01' in having a faster growth habit, a much taller plant height (reaching 8 to 15 meters in height), and in not flowering until the plants are ten years in age. There are no other cultivars of *Jacaranda mimosifolia* known to the Inventor.

BRIEF DESCRIPTION OF THE DRAWINGS

The accompanying colored photographs illustrate the overall appearance and distinct characteristics of the new *Jacaranda*, 'Sakai01'. The photographs were taken of a two year-old plant as grown outdoors in a 17-cm container in Boskoop, The Netherlands.

The photograph in FIG. 1 provides a side view of the plant habit of 'Sakai01'.

Figure 1:
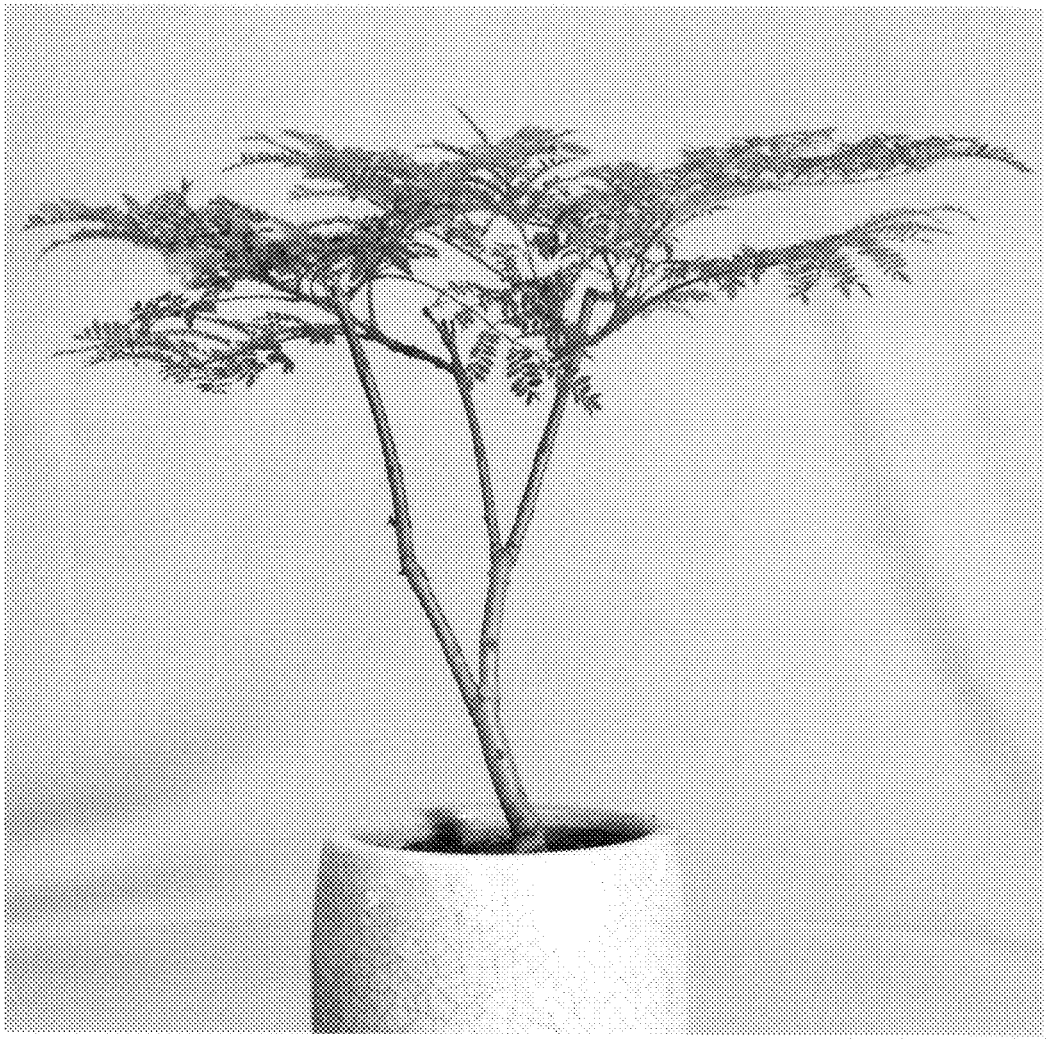
Figure 2:
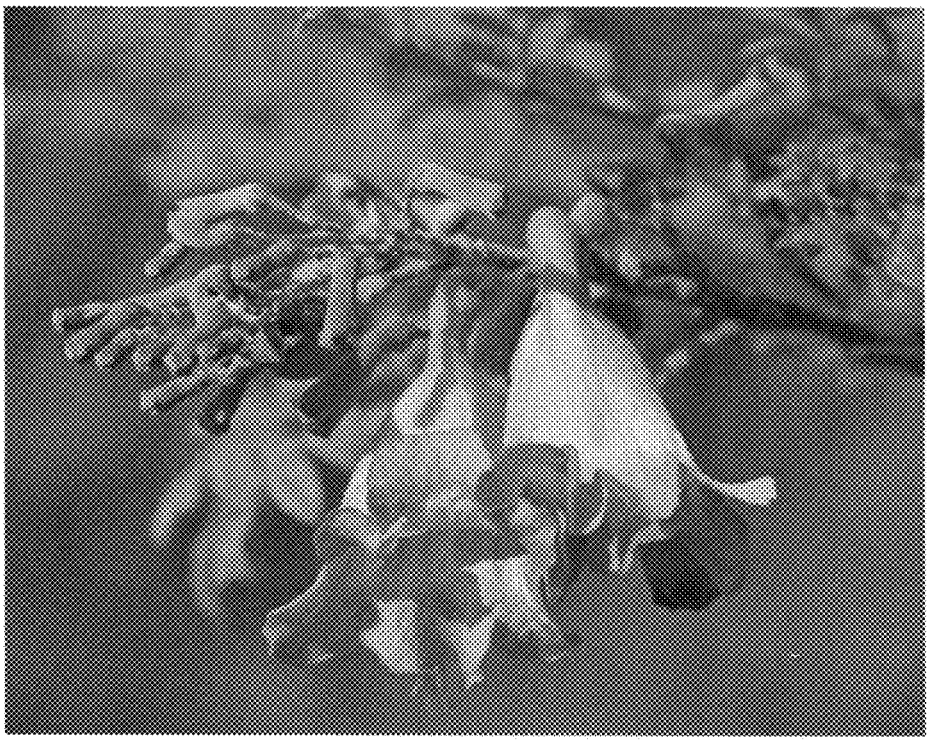

The photograph in FIG. 2 provides a close-up view of an inflorescence of 'Sakai01'.

Figure 3:
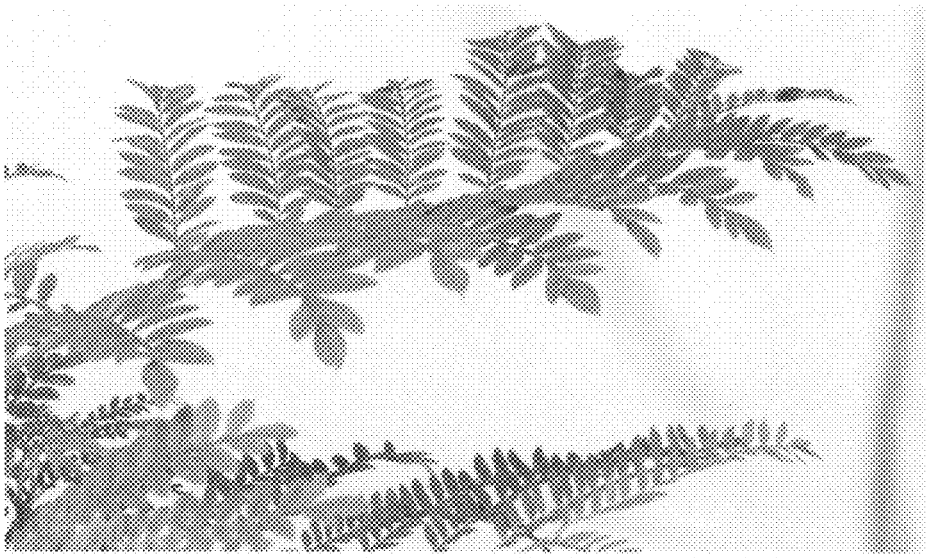

The photograph in FIG. 3 provides a close-up view of foliage of 'Sakai01'.

The colors in the photographs are as close as possible with the digital photography and printing techniques utilized and the color codes in the detailed botanical description accurately describe the new *Jacaranda.*

DETAILED BOTANICAL DESCRIPTION

The following is a detailed description of the new cultivar taken from two year-old plants as grown outdoors in a 17-cm container in Boskoop, The Netherlands. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Plant type.*—Sub-tropical tree; can be deciduous to evergreen depending on climate.

*Growth habit.*—Broad upright with domed crown.

*Height and spread.*—An average of 45.5 cm in height and 56 cm in spread and matures to a height of 2 to 3 meters and 1 m in spread in the landscape.

*Cold hardiness.*—U.S.D.A. Zones 9.

*Diseases and pests.*—No susceptibility or resistance to pests or diseases has been observed.

*Root description.*—Fine and fibrous.

*Growth rate.*—Slow.

*Propagation.*—Budding and grafting.

Stem description:

*Shape.*—Rounded.

*Stem size.*—Up to 5 lateral branches; average of 5 mm in diameter and 5.1 cm in length, main stems are about 2 cm in width measured 3 cm from base.

*Stem surface.*—Slightly glossy and smooth.

*Branching.*—Moderate to freely branching.

*Stem strength.*—Very Strong.

*Branch arrangement.*—Opposite.

*Branch aspect.*—Main stems upright, lateral stems held at an average angle of 70° from the main stems with flat sprays that spread upward and outward.

*Internode length.*—Average of 1.4 cm.

*Stem color.*—Immature branches are 144A, mature branches are 197C to 197D.

Foliage description:

*Leaf arrangement.*—Opposite.

*Leaf shape.*—Oblong.

*Leaf division.*—Bipinnate.

*Leaf base.*—Attenuate.

*Leaf apex.*—Short mucronate.

*Leaf venation.*—Pinnate, color: upper side 143A, lower side 138C.

*Leaf margins.*—Entire.

*Leaf surface.*—Both surfaces dull.

*Leaf color.*—Mature upper surface; 143A, mature lower surface; between 138B and 143B, mature lower surface: 143A; new growth upper surface; 143B, new growth lower surface; 144B in color.

*Leaf size.*—An average of 21.3 cm in length and 12.5 cm in width.

*Leaf quantity.*—About 6 per lateral branch (3 pairs).

*Leaflet shape.*—Elliptic.

*Leaflet size.*—An average of 1.3 cm in length and 6 mm in width.

*Leaflet quantity.*—Average of 400 per leaf.

*Petiole.*—Average length of leaf petiole (from base to lowest leaflet) is 3.4 cm, average length of rachis (from lowest leaflet to top of rachis) is 15.1 cm, average diameter of leaf petiole is 3 mm, average diameter of rachis (measured in the middle) is 2 mm, petiole color is 144A, rachis color is 144A to 144B, leaflets are sessile, smooth surface.

Inflorescence description:

*Inflorescence type.*—Axillary and terminal panicles.

*Inflorescence size.*—Average of 10.8 cm in height and 7.9 cm in width.

*Flower buds.*—Narrowly obovate in shape, an average of 2.6 cm in length and 8 mm in diameter, 90B to 90C in color.

*Flower fragrance.*—None.

*Lastingness of flowers.*—About 5 days.

*Flower aspect.*—Outward.

*Flower quantity.*—An average of 2 per lateral stem.

*Flower shape.*—Tubular-campanulate, typical for *Jacaranda.*

*Flower type.*—Single, tubular-campanulate.

*Flower size.*—Average of 3.1 cm in didmeter and 4.5 cm in depth.

*Peduncles.*—Average of 9.1 cm in length and 2.5 mm in diameter, strong, average angle of 0° to the lateral branch, strong in strength and 143A in color.

*Pedicels.*—Average of 6 mm in length and 1 mm in diameter, held at 15°, moderately strong in strength and 144A in color.

*Calyx.*—Rotate in shape, an average of 3 mm in length and 4 mm in diameter.

*Sepals.*—5, ovate in shape, acute apex, broad cuneate base, entire margin, an average of 3 mm in length and 1 mm in width, rotate in arrangement, both surfaces smooth and dull, color: young and mature upper and lower surface; 144A.

*Petals.*—6, lower 80% fused into tube, narrow oblong in shape, margin entire, apex obtuse, an average of 4.5 cm in length, 1.3 cm in width (measured at the base of the free part), overall appearance of the petal is smooth and dull and fused into a tubular-campanulate shape, when opening upper side; 90D with blotching of NN155D, when opening lower side; 91A, when fully opened upper side; 90D with a blotching of NN155D, when fully opened lower side; a blend of N88C, N88D and 91A.

Reproductive organs:

*Gynoecium.*—1 pistil, about 2.4 cm in length, style is an average of 2.2 cm in length, and 157D in color, stigma is club-shaped and plumose and 155C in color, ovary is N186D in color.

*Androcoecium.*—5 stamens, anthers are basifixed and narrow oblong in shape, 3 mm in length and 173D in color, filaments are an average of 1.5 cm in length and 157D in color, pollen is very low in quantity and 155A in color.

*Fruit and seed.*—No fruit or seed production has been observed to date.

It is claimed:

1. A new and distinct cultivar of *Jacaranda* plant named 'Sakai01' as herein illustrated and described.

* * * * *